United States Patent [19]
Carroll

[11] Patent Number: 6,123,917
[45] Date of Patent: Sep. 26, 2000

[54] METHOD FOR MAKING COCAINE RECEPTOR BINDING LIGANDS AND INTERMEDIATES THEREFOR

[75] Inventor: Frank Ivy Carroll, Durham, N.C.

[73] Assignee: Research Triangle Institute, Research Triangle Park, N.C.

[*] Notice: This patent is subject to a terminal disclaimer.

[21] Appl. No.: 08/509,055

[22] Filed: Jul. 31, 1995

Related U.S. Application Data

[62] Continuation-in-part of application No. 08/164,576, Dec. 10, 1993, Pat. No. 5,496,953, which is a continuation-in-part of application No. 07/792,648, Nov. 15, 1991, abandoned, which is a continuation-in-part of application No. 07/564,755, Aug. 9, 1990, Pat. No. 5,128,118, and a continuation-in-part of application No. 07/972,472, filed as application No. PCT/US91/05553, Aug. 9, 1991.

[51] Int. Cl.[7] .................. A61K 51/04; C07D 451/02; C07D 401/00
[52] U.S. Cl. .................. 424/1.85; 546/124; 546/125; 546/132
[58] Field of Search .................. 424/1.85; 546/124, 546/125, 132

[56] References Cited

U.S. PATENT DOCUMENTS

| | | | |
|---|---|---|---|
| 3,651,115 | 3/1972 | Belsky et al. | 260/448.2 |
| 3,813,404 | 5/1974 | Clarke et al. | 260/292 |
| 5,128,118 | 7/1992 | Carroll et al. . | |
| 5,380,848 | 1/1995 | Kuhar et al. . | |
| 5,413,779 | 5/1995 | Kuhar et al. . | |
| 5,496,953 | 3/1996 | Kuhar et al. . | |

OTHER PUBLICATIONS

Kimes et al., *J. Med. Chem.*, 35, pp. 4683–4689, 1992.
Carroll et al., *J. Med. Chem.*, 34, pp. 2719–2725, 1991.
Jacob et al., *Synthesis*, pp. 611–614, Jun. 1993.

*Primary Examiner*—Gary E. Hollinden
*Attorney, Agent, or Firm*—Oblon, Spivak, McClelland, Maier & Neustadt, P.C.

[57] ABSTRACT

An improved method for preparation of cocaine receptor binding ligands is provided. The method calls for the preparation of the silylaryl intermediate prepared from phenyl trimethylsilane and a anhydroecgonine methyl ester appropriately substituted. The intermediate is prepared in high purity and can be directly converted to the binding ligand by iodine substitution.

5 Claims, No Drawings

METHOD FOR MAKING COCAINE RECEPTOR BINDING LIGANDS AND INTERMEDIATES THEREFOR

DISCLOSURE OF PARENT APPLICATIONS

This application is a continuation-in-part application of Ser. No. 08/164,576, filed Dec. 10, 1993, now U.S. Pat. No. 5,496,953; which is in turn a continuation-in-part of Ser. No. 07/792,648, filed Nov. 15, 1991, now abandoned; which is in turn a continuation-in-part of Ser. No. 07/564,755, filed Aug. 9, 1990, now U.S. Pat. No. 5,128,118 and also a continuation-in-part of PCT/US91/05553, filed Aug. 9, 1991, the national phase of which is U.S. Ser. No. 07/972,472, now U.S. Pat. No. 5,413,779; all of which are incorporated herein by reference in their entirety.

FIELD OF THE INVENTION

This invention is directed to a class of binding ligands for cocaine and other receptors in the brain. Specifically, a new method of making novel and unobvious compounds showing high binding specificity and activity, and, in a radiolabeled form, can be used to bind these receptors, is provided. The compounds produced by the method are useful in biochemical assays, imaging techniques, and in a wide variety of drug treatment methodologies. Both a new synthetic method, and a key intermediate, are provided.

In U.S. application Ser. No. 07/564,755, there is disclosure of a family of compounds exhibiting particularly high specificity and affinity for cocaine receptors and other neurotransmitter receptors in the brain of the formula:

Where the broken line represents an optional chemical bond and the substituents at 2 and 3 may be at any position;

The iodo substituent may be at o, m, p, or multisubstituted;

$R_1 = CH_3$, $CH_2CH=CH_2$, $(CH_2)_n C_6 H_5$ n=1–4;
$R_2 = CH_3$, $C_2H_5$, $CH_3(CH_2)_3$, $(CH_3)_2CH$, $C_6H_5$, $C_6H_5CH_2$, $C_6H_5(CH_2)_2$;
X=pharmacologically acceptable anion

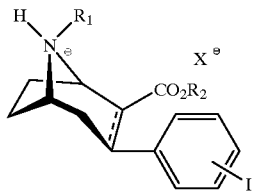

Sites of specific interest included cocaine receptors associated with dopamine transporter sites.

Subsequently, in the U.S. PCT Application from which priority is claimed, PCT/US91/05553, now U.S. Pat. No. 5,413,779 and which is incorporated herein by reference, the values for $R_1$ and $R_2$ were expanded, such that $R_1$ may be an alkyl of 1–7 carbon atoms, $CH_2CR_3=CR_4R_5$ wherein $R_3-R_5$ are each, independently $C_{1-6}$ alkyl, or phenyl compounds of the formula $C_6H_5(CH_2)_y$, wherein y=1–6. The PCT filing also reveals the affinity of these compounds for cocaine receptors associated with serotonin transporters, and confirms, for the first time, that the in vitro binding reported in the earlier-filed application, is confirmed in in vivo testing. Specific disclosure for a variety of applications, including using the receptors in both PET and SPECT scanning, wherein either the iodine substituent, or one of the carbon groups is radioactive (I-123, 125 or 131 and C11) thus providing methods for scanning the presence of specific cocaine receptors appears. Such scanning processes may be used to determine physiological conditions, such as Parkinson's Disease, to examine in general the density and distribution of specific cocaine receptors in various parts of the brain and/or body, to determine the efficacy of neurological treatments aimed at halting or reversing the degeneration of specific nerves in the brain, and screening drugs, such as antidepressant drugs.

The affinity of these compounds, as reported in the applications incorporated, is surprisingly high, and compared with prior art compounds, such as [$^3$H]WIN 35,428, the novel compounds of these applications exhibit extremely low $IC_{50}$ values for binding inhibition.

The immediate parent application, now U.S. Pat. No. 5,496,953 incorporated herein by reference, discloses related compounds of a formula

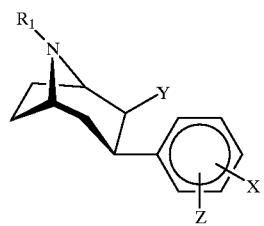

Wherein Y=$CH_2R_3$, $CO_2R_2$, $CONRR^1$, or

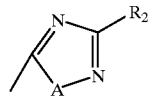

$R_1$=hydrogen, $C_{1-5}$ alkyl,
$R_2$=hydrogen, $C_{1-6}$ alkyl, $C_{3-8}$ cycloalkyl, $C_{1-4}$ alkoxy, $C_{1-6}$ alkynyl, halogen or amine,
$R_3$=OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl $OCOC_{1-3}$ alkylaryl,
A=S, O or N
X=H, $C_{1-6}$ alkyl, $C_{3-8}$ cycloalkyl, $C_{1-4}$ alkoxy, $C_{1-6}$ alkynyl, halogen, amino acylamido,
and
Z=H, I, Br, Cl, F, CN, $CF_3NO_2$, $N_3$, $OR_1$, $CO_2NH_2$, $CO_2R_1$, $C_{1-6}$ alkyl, $NR_4R_5$, $NHCOF_5$, $NHCO_2R_6$,
wherein $R_4-R_6$ are each $C_{1-6}$ alkyl,
R and $R^1$ are independently H, $C_{1-6}$ alkyl, $C_{1-6}$ alkene, $C_{1-6}$ alkyne, phenyl, phenyl substituted with 1–3 of $C_{1-6}$ alkyl, alkene, alkyl or alkoxy, $C_{1-6}$ alkoxy, phenoxy, amine, amine substituted with 1–2 of $C_{1-6}$ alkyl, alkene, alkyne, alkoxy or phenyl or phenoxy or R and $R^1$ may combine to form heterocyclic structure including pyrrolidinyl, piperidinyl and morpholino moieties, unsubstituted or substituted with 1–2 $C_{1-6}$ alkyl, alkene, alkyne or alkoxy groups.

These compounds exhibit unusually high affinity for binding to receptors for the dopamine transporter site, as well as the serotonin transporter site, again based on inhibition of [$^3$H]WIN 35,428 binding.

The most efficient method for preparation of the compounds of the family of binding ligands discussed above is through a tri-methylstannyl precursor, referred to as RTI-89. This intermediate or precursor is prepared from anhydroecgonine methyl ester in three steps. The intermediate is a focus of the grandparent application, U.S. application Ser.

No. 07/792,648 now abandoned. As the anhydroecgonine methyl ester is the most closely related commercially available compound, it is an object of those of ordinary skill in the art to provide a more direct and facile synthesis of the binding ligands described herein than the three-step synthesis leading to RTI-89. Additionally, it would be desirable to be able to provide an intermediate for the preparation of RTI-55 and the related compounds described above in a state of higher purity than the intermediate RTI-89, or its tri-butyl analogue which is also known in the art.

SUMMARY OF THE INVENTION

The above-described objects, and other objects developed hereinbelow, are achieved through the synthesis of an intermediate designated RTI-W148-1, which compound has the structure:

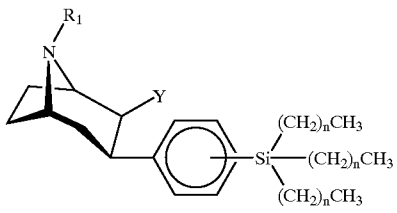

wherein n=0–4

$R_1$ is alkyl of 1–7 carbon atoms, alkene of 1–7 carbon atoms; phenyl, unsubstituted or substituted with an alkyl of 1–4 carbon atoms, Y is $CHR_3$, $CO_2R_3$, $CONR_4R_5$ or

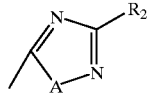

wherein $R_2$=H, $CH_3$, $C_2H_5$, $CH_3(CH_2)_3$, $(CH_3)_2CH$, $C_6H_5$, $C_6H_5CH_2$, $C_6H_5(CH_2)_2$, $C_{3-8}$ cycloalkyl, $C_{1-4}$ alkoxy, $C_{1-6}$ alkynyl, halogen (preferably Cl, Br or I), or amine;

$R_3$=OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl, $OCOC_{1-3}$ alkylaryl, wherein $R_4$ and $R_5$ are independently H, $C_{1-6}$ alkyl, $C_{1-6}$ alkene, $C_{1-6}$ alkyne, phenyl, phenyl or amine substituted with 1–3 of $C_{1-6}$ alkyl, alkene or alkoxy, or is $C_{1-6}$ alkoxy, phenoxy, amine, or $R_4$ and $R_5$ may combine to form heterocyclic moieties including pyrrolidinyl, piperidinyl and morpholino, unsubstituted or substituted with 1–2 $C_{1-6}$ alkyl, alkene, alkyne or alkoxy groups, wherein A=S, O or N.

This intermediate may be quickly converted to the binding ligands of the above-described class by iodine exchange using ICl and silver tetrafluoroborate. Where imaging or assay purposes are intended, the iodine is radioactive, i.e., $^{123}I$, $^{125}I$ or $^{131}I$. Where, instead, pharmaceutical uses are intended, such as a substitute for methadone and similar drug treatments, or other pharmaceutical ends, non-radioactive ICl may be used.

DETAILED DESCRIPTION OF THE INVENTION

The arylsilane intermediate of this invention is prepared quickly and conveniently from conventional starting materials, in a high degree of purity. It is quickly converted to the binding ligands described in the parent application for tracing (SPECT or PET) if desired, by iodination using ICl. The invention is exemplified herein with the identities of substituents $R_1$–$R_5$, A and n, selected so as to give the prototypical and commercialized radioactive binding ligand RTI-55, which has the formula

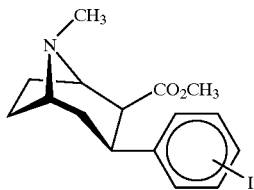

As those of skill in the art will recognize, the identities for $R_1$–$R_5$, Y and A may be readily substituted into the starting materials used to prepared RTI-W148-1, as the starting material, the methylester, is readily substituted on, see, e.g., Clarke, J. Med. Chem. 16, 1260 (1973).

EXAMPLE

3β[4-Trimethylsilyl)phenyl]-2β-carboxylic Acid Methyl Ester (RTI-W148-1):

p-Iodophenyltrimethylsilane was synthesized according to literature procedures.[1] The aryl halide (1.633 g, 6.02 mmol) was added gradually to Mg turnings (0.317 g, 13.04 mmol) and an $I_2$ crystal under $N_2$. Once the vigorous reaction had subsided, the Grignard was refluxed for 0.5 hr. The reagent was cooled to room temperature and transferred into a round bottom flask under $N_2$. The standard procedure for the synthesis of other 3β-(phenyl)tropane analogues was used as follows:[2] The reaction vessel was cooled to −40° C. and a solution of anhydroecgonine methyl ester (0.226 g, 1.24 mmol) in 15 mL anhydrous ether was added dropwise over 10 min. The reaction was cooled to −78° C. and a solution of trifluoroacetic acid (1 mL) in 10 mL EtO was added dropwise over 10 minutes. The reaction mixture was warmed to 0° C. and water (25 mL) was added. If necessary, the aqueous layer was acidified to pH 2 (with conc. HCl) and the layers were separated. The aqueous layer was basified to pH 11 with $NH_4OH$ and filtered through celite. The aqueous layer was extracted with $Et_2O$ (4×50 mL). The organic layers were combined and dried over $MgSO_4$. The solvent was removed under reduced pressure to afford 0.40 g of a cloudy oil.

[1] Jacob, L. a.; Chen. B. -L.; Stec, D., *Synthesis*, 1993, 611–614.
[2] Carroll, F. I., Gao, Y., Rahman, A.; Abraham, P., Parham. K.; Lewin, A. H.; Boja. J. W.; Kuhar, M. J., *J. Med Chem.*, 1991, 34, 2719–2725.

Purification was accomplished using flash chromatography (9/1 $Et_2O/Et_3N$ diluted with 50% hexanes). The fractions were pooled to give 0.202 g (49.3% yield) of the RTI-W148-1 as a white solid. A second fraction (0.023 g) contained a mixture of the α and β-isomers. Recrystallization of the β-isomer (0.182 g) from petroleum ether afforded 0.155 g of product, mp. 117–119° C.

Synthesis of RTI-55 from RTI-148-1:

To a solution of 58 mg of RTI-148-1 in 4 mL of methanol was added 124 mg of silver tetrafluoroborate. The mixture was cooled to 0° C., and 0.64 mL of a 1.0 M solution of ICl in methanol was added. The reaction was allowed to warm to 25° C. and kept at that temperature for 2 h. The reaction mixture was diluted with water, basified with $NH_4OH$, and extracted with $CH_2Cl_2$. Evaporation of the solvent gave 70 mg of RTI-55. Flash chromatography gave 60 mg (90%) of RTI-55.

Synthesis of 3β[4-Trimethylsilyl)Phenyl]-2β-Carboxylic Acid Methyl Ester (RTI-W148-1)

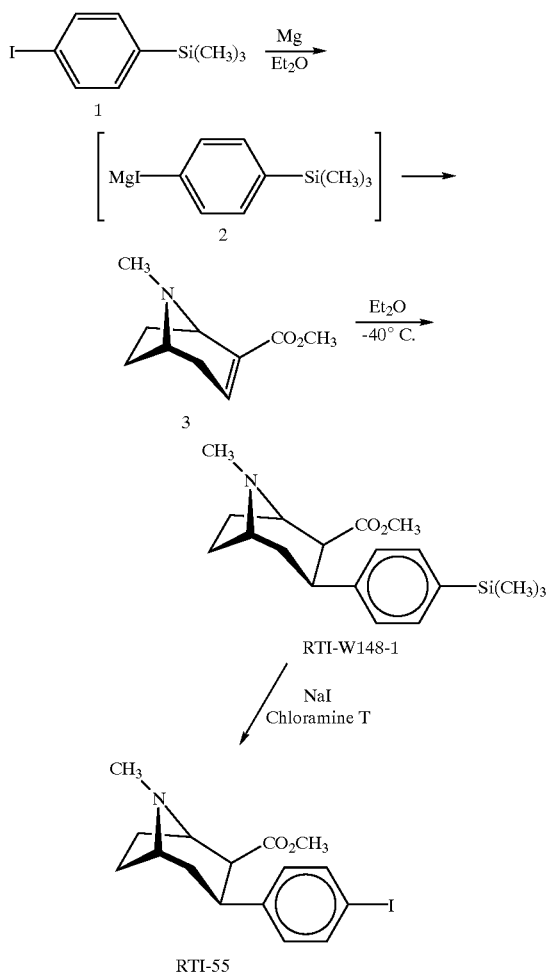

This invention has been described in both generic terms, and by reference to a specific description. No specific description or example is considered binding, unless so identified. Alternate forms and conditions will occur to those of ordinary skill in the art, without the exercise of inventive faculty, and remain within the scope of this invention, save as limited by the claims set forth below.

What is claimed is:

1. A compound of the formula:

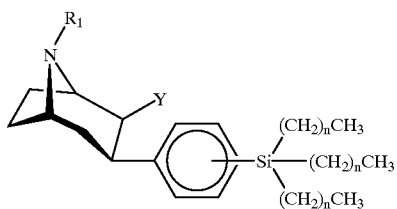

wherein
n=0–4
$R_1$ is alkyl of 1–7 carbon atoms, alkene of 1–7 carbon atoms; phenyl, unsubstituted or substituted with an alkyl of 1–4 carbon atoms,
Y is $CHR_3$, $CO_2R_2$, $CONR_4R_5$ or

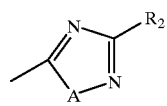

wherein
$R_2$=H, $CH_3$, $C_2H_5$, $CH_3(CH_2)_3$, $(CH_3)_2CH$, $C_6H_5$, $C_6H_5CH_2$, $C_6H_5(CH_2)_2$, $C_{3-8}$ cycloalkyl, $C_{1-4}$ alkoxy, $C_{1-6}$ alkynyl, halogen, or amine;
$R_3$=OH, hydrogen, $C_{1-6}$ alkyl, $C_{3-8}$ cycloalkyl, $C_{1-4}$ alkoxy, Cl, Br, I, CN, $NH_2$, $NHC_{1-6}$ alkyl, $NC_{1-6}$ alkyl, $OCOC_{1-6}$ alkyl, $OCOC_{1-3}$ alkylaryl,
wherein $R_4$ and $R_5$ are independently H, $C_{1-6}$ alkyl, $C_{1-6}$ alkene, $C_{1-6}$ alkyne, phenyl, phenyl or amine substituted with 1–3 of $C_{1-6}$ alkyl, alkene or alkoxy, or is $C_{1-6}$ alkoxy, phenoxy, amine, or $R_4$ and $R_5$ may combine to form heterocyclic moieties including pyrrolidinyl, piperidinyl and morpholino, unsubstituted or substituted with 1–2 $C_{1-6}$ alkyl, alkene, alkyne or alkoxy groups, wherein A=S, O or N.

2. A method of preparing cocaine receptor binding ligands comprising:
   reacting a solution of the compound of claim 1 in methanol with ICl in the presence of silver tetrafluoroborate, and maintaining the reaction at room temperature for a time sufficient to permit conversion to an iodinated cocaine receptor binding ligand.

3. The method of claim 2, wherein silver tetrafluoroborate is added to a methanol solution of the compound of claim 1, the resulting solution being cooled to 0° C., and ICl is added thereto.

4. The method of claim 3, wherein the reaction product resulting is extracted with $CH_2Cl_2$ to recover a cocaine receptor binding ligand.

5. The compound of claim 1, wherein $R_2$ is chlorine or iodine.

* * * * *

UNITED STATES PATENT AND TRADEMARK OFFICE
CERTIFICATE OF CORRECTION

PATENT NO. : 6,123,917
DATED : September 26, 2000
INVENTOR(S) : Frank I. Carroll Page 1 of 1

It is certified that error appears in the above-identified patent and that said Letters Patent is hereby corrected as shown below:

Column 1,
Lines 32-40, should be placed after the formula on line 30.

Column 3,
Line 31, "alkyl of 1-4 carbon atoms," should read -- alkyl of 1-4 carbon atoms, wherein said silane substituent is O, M, or P: --

Column 4,
Line 65, "CII$_2$Cl$_2$" should read -- CH$_2$Cl$_2$ --.

Column 5,
Line 13, 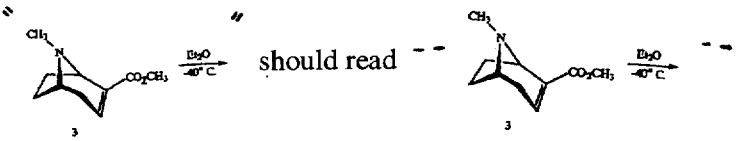 should read

Column 6,
Line 9, 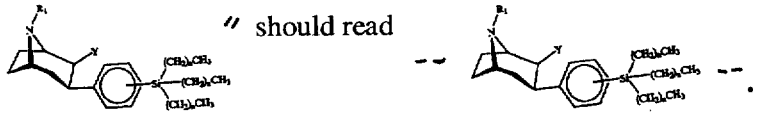 should read

Line 17, "CIIR$_3$" should read -- CH$_2$R$_3$ --.

Signed and Sealed this

Twenty-seventh Day of November, 2001

Attest:

NICHOLAS P. GODICI
Attesting Officer    Acting Director of the United States Patent and Trademark Office